United States Patent
Govari

(10) Patent No.: US 11,077,288 B2
(45) Date of Patent: Aug. 3, 2021

(54) FLUSHING BALLOON CATHETER FOR OBSERVATION AND REMOVAL OF CLOTS UNDER VESSEL BIFURCATION CONDITIONS

(71) Applicant: Biosense Webster (Israel) Ltd., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 364 days.

(21) Appl. No.: 16/192,203

(22) Filed: Nov. 15, 2018

(65) Prior Publication Data

US 2020/0155814 A1 May 21, 2020

(51) Int. Cl.
| | | |
|---|---|---|
| *A61M 25/10* | (2013.01) | |
| *A61B 1/00* | (2006.01) | |
| *A61B 1/313* | (2006.01) | |
| *A61B 17/22* | (2006.01) | |
| *A61B 1/045* | (2006.01) | |
| *A61B 5/02* | (2006.01) | |

(52) U.S. Cl.
CPC ....... *A61M 25/104* (2013.01); *A61B 1/00082* (2013.01); *A61B 1/3137* (2013.01); *A61B 17/22012* (2013.01); *A61B 1/00096* (2013.01); *A61B 1/045* (2013.01); *A61B 5/02007* (2013.01); *A61B 2017/22065* (2013.01); *A61B 2017/22079* (2013.01); *A61M 25/1002* (2013.01); *A61M 2025/1043* (2013.01)

(58) Field of Classification Search
CPC ........ A61M 25/104; A61M 2025/1045; A61B 1/00082; A61B 1/3137; A61B 1/00096; A61B 1/045; A61B 17/22012; A61B 5/02007

See application file for complete search history.

(56) References Cited

U.S. PATENT DOCUMENTS

| | | |
|---|---|---|
| 4,445,892 A | 5/1984 | Hussein et al. |
| 5,007,898 A | 4/1991 | Rosenbluth et al. |
| 6,575,932 B1 | 6/2003 | O'Brien et al. |
| 6,582,448 B1 | 6/2003 | Boyle et al. |
| 6,702,782 B2 | 3/2004 | Miller et al. |
| 7,588,535 B2 | 9/2009 | Adler et al. |

(Continued)

OTHER PUBLICATIONS

European Search Report for Application No. 19209085.0, dated Apr. 17, 2020.

(Continued)

*Primary Examiner* — Nathan R Price
*Assistant Examiner* — Dung T Ulsh
(74) *Attorney, Agent, or Firm* — Eugene L. Szczecina, Jr.

(57) ABSTRACT

A catheter includes a shaft, a sealing balloon, a bifurcation sealing element and a camera. The shaft has a distal end for insertion into a clotted blood vessel of a brain of a patient. The sealing balloon, which is fitted at a proximal section of the distal end, is configured to proximally seal a portion of the clotted blood vessel. The bifurcation sealing element is fitted at the distal end, distally to the sealing balloon, and is configured to seal a bifurcation located at the proximally sealed portion of the clotted blood vessel. The camera, which is fitted at a distal edge of the distal end, is configured to visually image a clot that clots the blood vessel.

11 Claims, 2 Drawing Sheets

(56) References Cited

U.S. PATENT DOCUMENTS

| | | |
|---|---|---|
| 2006/0206188 A1 | 9/2006 | Weber et al. |
| 2006/0271090 A1 | 11/2006 | Shaked et al. |
| 2008/0086193 A1* | 4/2008 | Thramann ................. A61F 2/07 |
| | | 623/1.13 |
| 2008/0200946 A1* | 8/2008 | Braun ............... A61M 25/0054 |
| | | 606/198 |
| 2010/0114019 A1* | 5/2010 | Dunn ....................... A61F 2/958 |
| | | 604/101.01 |
| 2011/0172697 A1* | 7/2011 | Jonsson ........... A61B 17/12036 |
| | | 606/194 |
| 2012/0089220 A1 | 4/2012 | Lualdi |
| 2015/0065945 A1* | 3/2015 | Zarins .................. A61K 31/475 |
| | | 604/21 |
| 2016/0206860 A1* | 7/2016 | Gupta ............. A61M 25/09041 |
| 2017/0056626 A1* | 3/2017 | Ischinger ............. A61M 25/104 |
| 2017/0215890 A1* | 8/2017 | Turjman ............. A61B 17/1204 |
| 2017/0265879 A1* | 9/2017 | Washburn, II ......... A61B 1/126 |

OTHER PUBLICATIONS

U.S. Appl. No. 62/675,952, filed May 24, 2018, entitled "Position Sensor on Brain Clot Sheath and Location Pad Collar."

* cited by examiner

FLUSHING BALLOON CATHETER FOR OBSERVATION AND REMOVAL OF CLOTS UNDER VESSEL BIFURCATION CONDITIONS

FIELD OF THE INVENTION

The present invention relates generally to medical probes, and particularly to catheters for cerebrovascular applications.

BACKGROUND OF THE INVENTION

Various types of medical probes, such as catheters, include optical and mechanical elements at a distal end of the probe. For example, U.S. Patent Application Publication 2017/0265879 describes an integrated clot evacuation device having visualization for use in neurosurgical applications, particularly for the evacuation of clots formed as a result of intracranial hemorrhage (ICH). The device may further include an integrated camera and light for visualizing the interior of the brain and the clot itself. Further, the device is configured to evacuate clots through aspiration and irrigation.

As another example, U.S. Pat. No. 4,445,892 describes a dual balloon catheter device that is provided with two spaced and expandable balloons for occluding a segment of a blood vessel. The device also includes a first channel for flushing the occluded segment, an optic system for use in the segment, and a second channel for introducing fluid into the blood vessel distally of the device.

U.S. Pat. No. 6,575,932 describes a local delivery device comprising a distal catheter unit and a proximal catheter unit which may be positioned by sliding over the distal catheter unit. Both the distal and the proximal catheter units have separate inflatable occluding balloons. The positioning of the catheter units by sliding in relation to each other provides for variable inter-balloon distances, which in turn provides for a variably sized occlusion region in a hollow tubular organ, for example a vessel. Dispersed on the catheter shaft between the two occluding balloons are multiple infusion ports through which therapeutic agents may be delivered to an occluded region of a hollow tubular organ. The local delivery device may further comprise a quantifying device for determining the distance between the two occluding balloons. Therefore, precise adjustment of the inter-balloon distance permits controlled delivery of therapeutics to a discreet length of the hollow tubular organ wall.

U.S. Pat. No. 5,007,898 describes an apparatus and method for the treatment of the symptoms of obstructive prostatism. The apparatus comprises an expandable dilatation catheter and an axially elongate sheath, adapted for transurethral insertion. Disposed near the proximal end of the expandable dilation portion of the catheter is a plurality of irrigation ports. A saline solution travels through an irrigation conduit and is secreted through the irrigation ports so as to flush away blood, etc., away from the lens of a cystoscope and provides the urologist with an unobstructed view of the dilation catheter and external urethral sphincter muscle.

U.S. Pat. No. 6,702,782 describes a balloon catheter having at least two lumens. One of the lumens is a large working lumen. The balloon catheter is especially useful as a guide catheter and may be used in a variety of therapeutic and diagnostic procedures. In particular, it has value in treating neurovascular embolic strokes in combination with other devices which are delivered to the stroke site through that working lumen. When intended for use in treating embolic stroke, the catheter may be a component of a kit including a foreign body retriever. Further, amongst other procedures, the invention includes methods of temporarily blocking a vascular lumen, of removing neurovascular or peripheral emboli.

U.S. Pat. No. 7,588,535 describes an apparatus, system and method for providing an image enhancing effect for a photographic image of a target region within an intravascular environment. The apparatus has a plurality of different embodiments, each of which reduces the ambient "noise" detected along with the light reflected from the target region in order to increase the signal/noise ratio, thereby to enhance the quality of the image produced. In an embodiment the intravascular environment is flushed with saline in order to enable video image capture.

SUMMARY OF THE INVENTION

An embodiment of the present invention provides a medical system including a shaft, a sealing balloon, a bifurcation sealing element and a camera. The shaft has a distal end for insertion into a clotted blood vessel of a brain of a patient. The sealing balloon, which is fitted at a proximal section of the distal end, is configured to proximally seal a portion of the clotted blood vessel. The bifurcation sealing element is fitted at the distal end, distally to the sealing balloon, and is configured to seal a bifurcation located at the proximally sealed portion of the clotted blood vessel. The camera, which is fitted at a distal edge of the distal end, is configured to visually image a clot that clots the blood vessel.

In some embodiments, the bifurcation sealing element includes a movable sealing plate.

In some embodiments, the distal end further includes an inflatable member configured to press the bifurcation sealing element against the bifurcation.

In an embodiment, the distal end further includes an elastic member configured to press the bifurcation sealing element against the bifurcation.

In another embodiment, the distal end further includes a working channel that is configured to guide a clot removal device.

In some embodiments, the distal end further includes a working channel that is configured to flow fluid into the proximally sealed portion.

In some embodiments, the distal end further includes a working channel that is configured to channel suction sub-pressure into the proximally sealed portion so as to draw the clot.

There is additionally provided, in accordance with an embodiment of the present invention, a catheterization method including inserting a shaft having a distal end into a clotted blood vessel of a brain of a patient. A portion of the clotted blood vessel is proximally sealed using a sealing balloon which is fitted at a proximal section of the distal end. A bifurcation located at the proximally sealed portion of the clotted blood vessel is sealed using a bifurcation sealing element which is fitted at the distal end, distally to the sealing balloon. A clot that clots the blood vessel is visually imaged using a camera which is fitted at a distal edge of the distal end.

The present invention will be more fully understood from the following detailed description of the embodiments thereof, taken together with the drawings in which:

DETAILED DESCRIPTION OF EMBODIMENTS

Overview

Figure 1:
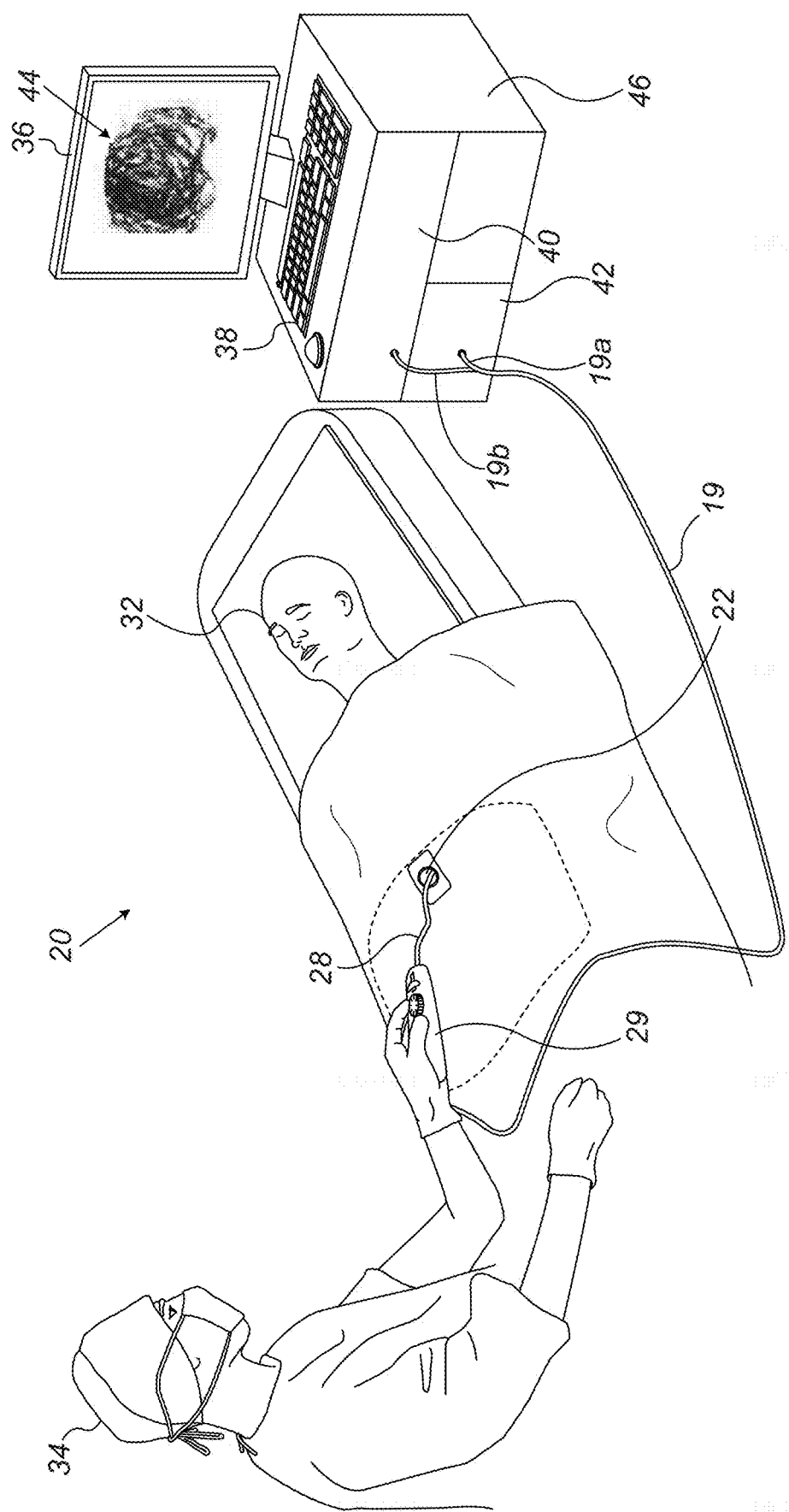
FIG. 1 is a schematic, pictorial illustration of a cerebrovascular catheter-based system for visual inspection of a clot and for clot removal, in accordance with an embodiment of the present invention.

An obstructing clot in a large blood vessel of the brain, such as an artery, is a medical emergency condition. The location of the clot in the brain may be detected with computed tomography (CT) or fluoroscopy imaging, using injection of a contrast agent. Such medical imaging methods, however, cannot visualize the clot.

Clear visualization of a clot may assist in determining the appropriate treatment method. For example, if a clot is evaluated by visual inspection to be relatively solid, a physician may attempt to remove the clot using a stent to grasp and retract it. If, on the other hand, visual inspection of the clot leads the physician to evaluate the clot as more wax-like, the physician may attempt to draw the clot out by suction.

A clot may be visually inspected during catheterization by, for example, capturing color images of the clot, after flushing obscuring blood from the clotted volume of the vessel with saline solution. Unfortunately, in some cases, a clot is formed in the immediate vicinity of a vessel bifurcation. The bifurcation hinders visual inspection of such a clot because continuous blood leakage from the split vessel obscures the clot. Since the physician cannot visually inspect the clot, and correspondingly determine a treatment method, the physician may need to guess which treatment method to use.

Embodiments of the present invention that are described hereinafter provide a catheter which enables a physician to visually inspect a clot under blood vessel bifurcation conditions. The disclosed catheter comprises (a) a shaft having a distal end for insertion into a clotted blood vessel of a brain of a patient, and (b) the following at a distal end of the shaft: a bifurcation-sealing element, such as a movable sealing sheet, to seal off a bifurcation; an expandable sealing balloon located at a proximal section of the distal end, to proximally seal a clotted portion of the vessel; one or more working channels that provide access to, for example, means for flushing the sealed portion of the blood vessel; and, a camera located at the distal edge of the distal end to visually image the clot.

In an embodiment, the catheter is inserted into the clotted artery until the camera is in visual range of the clot. The sealing balloon is expanded so as to proximally seal an artery portion between the camera and the clot. The movable sealing sheet, which is typically configured to seal a bifurcation of sizes of one (1) to ten (10) millimeters, is deployed to seal off the bifurcation so as to establish a sealed portion of the artery. The sealed portion (i.e., artery volume) is then flushed with, for example, saline solution pumped through one or more of the working channels so as to replace blood in the volume with saline. The saline, which is transparent in the visual range, enables the camera to acquire color images of the clot. The color images are typically displayed to the physician on a monitor.

In some embodiments, after visually inspecting the clot and determining its physical properties, the physician uses a working channel to perform a corresponding treatment. For example, if the physician determines, based on the images, that the clot is solid-like, the physician may advance a clot removal device, such as a stent, through a working channel to grasp and retract the clot. On the other hand, if the physician concludes, based on the images, that the clot is very soft (e.g., gel-like and pliable), the physician may apply suction sub-pressure into the sealed portion, so as to draw the clot through the working channel.

The disclosed catheter and visual inspection technique enables a physician to visually inspect and evaluate a clot's physical properties under bifurcation conditions. Thus, the disclosed technique increases the probability of successfully removing a clot in a complex case where a bifurcation of arteries exists in the immediate vicinity of the clot. Therefore, the enclosed catheter and method may improve the clinical outcome of a medical emergency catheterization procedure for the elimination of a brain clot.

System Description

FIG. 1 is a schematic, pictorial illustration of a cerebrovascular catheter-based system 20 for visual inspection and removal of a clot, in accordance with an embodiment of the present invention.

A catheter controller handle 29, held by a physician 34 operating system 20, is connected to a proximal end of a catheter 28. Controller handle 29 allows the physician to advance and navigate catheter 28 in the brain, for example through an entry point 22 at a thigh artery of patient 32. Physician 34 uses operating controls on handle 29 to seal a clotted region of an artery, by inflating a sealing balloon and by blocking any bifurcation using a sealing sheet, as described below.

Next, the physician operates a pumping unit 42 to flush the sealed portion with saline through a pipe 19a that is connected on a proximal end to pumping unit 42 and on a distal end to a proximal end of a working channel running through catheter 28, described below, via a valve in handle 29.

Electrical signals from catheter 28 are sent via a cable 19b. Pipe 19a and cable 19b are included in a cable 19 that connects to catheter 28 via handle 29. The physician then acquires a visual image 44 of the brain clot using a camera fitted at the distal end of catheter 28. Images of the brain clot are presented on a screen 36. Subsequent to the clot visualization process, and based on the images, physician 34 assesses the clot's physical properties and determines the appropriate treatment.

Elements of system 20 are controlled by a system processor 40. Processor 40 may be mounted in a console 46, which comprises operating controls 38 that typically include a keypad and/or a pointing device such as a mouse or trackball. Processor 40 uses software stored in a memory to operate system 20. The software may be downloaded to processor 40 in electronic form, over a network, for example, or it may, alternatively or additionally, be provided and/or stored on non-transitory tangible media, such as magnetic, optical, or electronic memory.

The system shown in FIG. 1 is chosen purely for the sake of conceptual clarity. Other system elements may comprise, for example, a magnetic catheter-based position tracking sub-system, such described in U.S. Provisional Patent Application 62/675,952, filed May 24, 2018, entitled "Position Sensor on Brain Clot Sheath and Location Pad Collar," which is assigned to the assignee of the present patent application and whose disclosure is incorporated herein by reference. Alternatively or additionally, an X-ray fluoroscopic brain imaging sub-system may be used. Handle 29 may contain additional elements, such as a valve and an entry point to the working channel to slide in a shaft that is fitted, at its distal end, with a therapeutic device, such as a clot removal stent.

Figure 2:
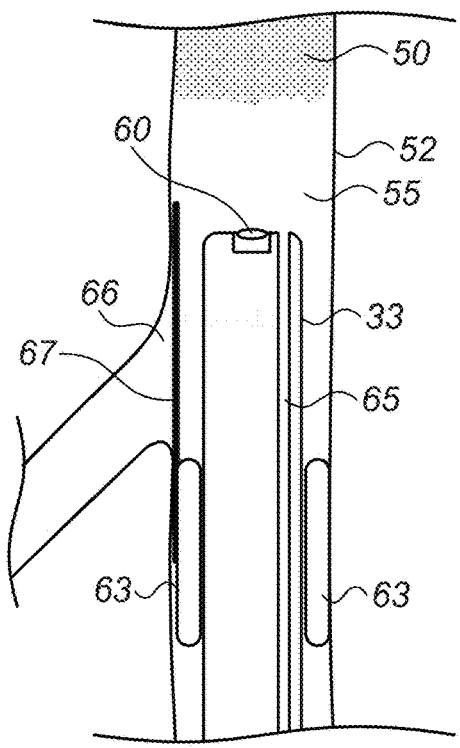
FIG. 2 is a view of a distal end of a catheter, which is configured to perform visual imaging of a clot, in accordance with an embodiment of the present invention.

Flushing Balloon Catheter to Observe and Remove Clot Under Vessel Bifurcation Conditions FIG. 2 is a view of a distal end 33 of catheter 28, which is configured to perform visual imaging of a clot 50, in accordance with an embodiment of the present invention. In the present example, distal end 33 comprises a camera 60, a sealing balloon 63 and a movable sealing sheet 67. One or more working channels 65 run through the catheter.

As seen, clot 50 blocks blood flow in an artery 52. Distal end 33 of catheter 28 was navigated and advanced by physician 34, to a position close enough to clot 50 to have camera 60 capture visual images of the clot (after obscuring blood has been cleared). Sealing balloon 63 is shown already inflated, proximally sealing an artery volume 55 between camera 60 and clot 50.

In some cases, as seen in FIG. 2, an artery bifurcation 66 prevents forming a sealed artery volume 55 with balloon 63 only. In some embodiments, distal end 33 incorporates and uses a bifurcation sealing element, such as movable sealing sheet 67, to seal off bifurcation 66, so as to prevent fresh blood flowing via the split artery from obscuring clot 50.

In some embodiments, after sealing sheet 67 is aligned with bifurcation 66, sealing sheet 67 is pressed against the artery wall using an inflatable member and/or an elastic element (not shown), or by mechanical manipulation, for example by using a transmission controlled from the catheter handle. Working channel 65 provides access to the fully sealed volume 55, which enables physician 34 stream saline into volume 55 in order to flush obscuring blood and have camera 60 acquire images of clot 50.

In some embodiments, after physician 34 has visually inspected the clot and, based on the visual inspection, determined the clot's physical properties, the physician selects a corresponding treatment method to eliminate clot 50. For example, if clot 50 is determined by physician 34 to be solid-like, then physician 34 advances a clot removal stent through working channel 65 to grasp and retract clot 50. If physician 34 determines that clot 50 is gel-like, physician 34 applies suction to draw clot 50 and/or infuse medication through working channel 65, in order to dissolve clot 50.

The example illustration shown in FIG. 2 is chosen purely for the sake of conceptual clarity. FIG. 2 shows only parts relevant to embodiments of the present invention. For example, catheter elements, such as those used for the deployment and support mechanism of bifurcation sealing sheet 67 are omitted. In some embodiments, physician 34 initially images bifurcation 67 using contrast agent-enhanced X-ray fluoroscopy imaging of artery 52. Sealing sheet 67 may be made of plastics such as PET, polystyrene or Pebax® elastomer, and may include a radiopaque marker.

Figure 3:
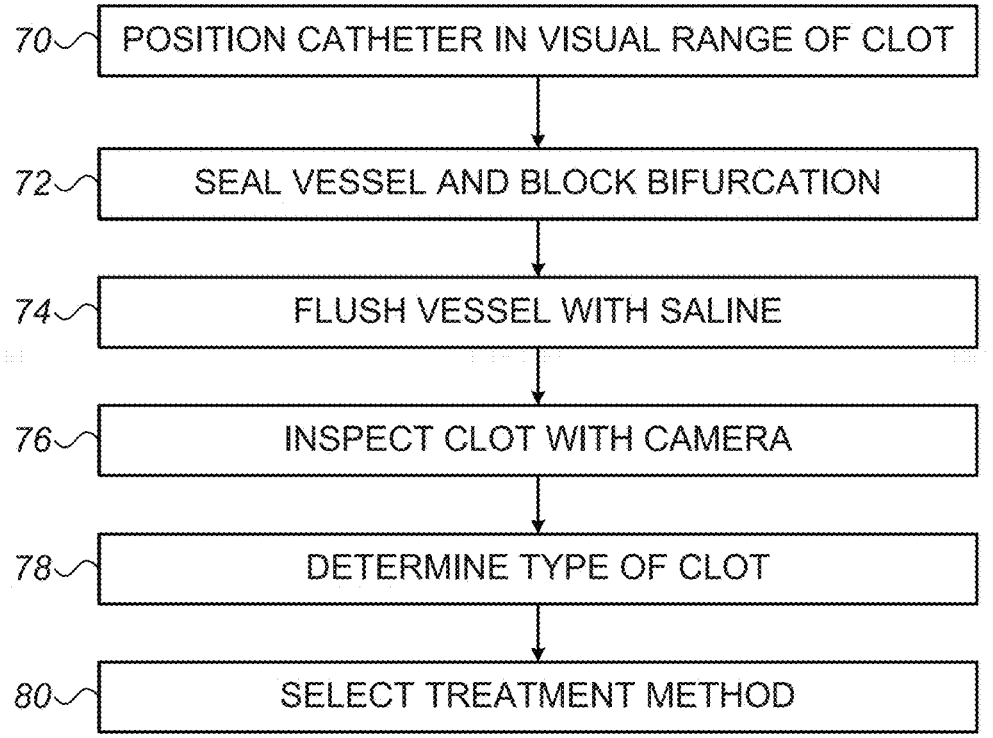
FIG. 3 is a flow chart that schematically illustrates a method for visualizing a clot and correspondingly selecting a treatment, in accordance with an embodiment of the present invention.

FIG. 3 is a flow-chart that schematically illustrates a method for visualizing a clot and correspondingly selecting a treatment, in accordance with an embodiment of the present invention. The process begins with physician 34 positioning distal end 33 of catheter 28 to visually inspect clot 50 with a camera 60, at a catheter positioning step 70. Next, at a sealing step 72, physician 34 seals a portion (i.e., region) of artery 52, by inflating balloon 63, and, in the case of an artery bifurcation 67, by additionally moving sealing sheet 67 to block the bifurcation. In a saline flushing step 74, physician 34 flows saline through working channel 65 to clear blood from the sealed portion of artery 52. Next, physician 34 operates camera 60 to acquire visual images of clot 60, at a clot inspection step 76. Based on the acquired images, physician 34 determines the physical properties of clot 50, such as its solid-like or gel-like composition. Finally, based on the determination of the physical properties of clot 50, physician 34 selects a treatment method to eliminate clot 50, at a treatment method selection step 80. For example, if the clot is solid-like, the physician may advance a clot removal stent to grasp and retract the clot. If, on the other hand, the clot is very soft, the physician may apply suction through working channel 65, so as to draw out clot 50.

The example flow chart shown in FIG. 3 is chosen purely for the sake of conceptual clarity. In alternative embodiments, for example, based on the indication from camera 60, physician 34 may choose to remove the clot by infusing medications at the clot site.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A catheter, comprising:
   a shaft having a distal end for insertion into a clotted blood vessel of a brain of a patient;
   a sealing balloon, which is fitted at a proximal section of the distal end, and is configured to proximally seal a portion of the clotted blood vessel;
   a bifurcation sealing element, which is fitted at the distal end, distally to the sealing balloon, and is configured to seal a bifurcation located at the proximally sealed portion of the clotted blood vessel, the bifurcation sealing element comprises a movable sealing plate; and
   a camera, which is fitted at a distal edge of the distal end and is configured to visually image a clot that clots the blood vessel.

2. The catheter according to claim 1, wherein the the sealing balloon is configured to press the bifurcation sealing element against the bifurcation.

3. The catheter according to claim 1, and comprising a working channel that is configured to guide a clot removal device.

4. The catheter according to claim 1, and comprising a working channel that is configured to flow fluid into the proximally sealed portion.

5. The catheter according to claim 1, and comprising a working channel that is configured to channel suction subpressure into the proximally sealed portion so as to draw the clot.

6. A catheterization method, comprising:
inserting a shaft having a distal end into a clotted blood vessel of a brain of a patient;
proximally sealing a portion of the clotted blood vessel using a sealing balloon which is fitted at a proximal section of the distal end;
sealing a bifurcation located at the proximally sealed portion of the clotted blood vessel using a bifurcation sealing element which is fitted at the distal end, distally to the sealing balloon, wherein sealing the bifurcation comprises sealing the bifurcation using a movable sealing plate; and
visually imaging a clot that clots the blood vessel using a camera which is fitted at a distal edge of the distal end.

7. The method according to claim 6, wherein sealing the bifurcation comprises pressing the bifurcation sealing element against the bifurcation using an inflatable member.

8. The method according to claim 6, wherein sealing the bifurcation comprises pressing the bifurcation sealing element against the bifurcation using an elastic member.

9. The method according to claim 6, and comprising guiding a clot removal device through a working channel in the shaft.

10. The method according to claim 6, and comprising flowing fluid into the proximally sealed portion through a working channel in the shaft.

11. The method according to claim 6, and comprising channeling suction through a working channel in the shaft, so as to draw the clot.

* * * * *